(12) United States Patent
Dudai

(10) Patent No.: US 8,617,188 B2
(45) Date of Patent: Dec. 31, 2013

(54) SURGICAL MESH, MESH INTRODUCING AND PLACING DEVICES AND METHODS

(76) Inventor: Moshe Dudai, Zikhron-Yaakov (IL)

( * ) Notice: Subject to any disclaimer, the term of this patent is extended or adjusted under 35 U.S.C. 154(b) by 515 days.

(21) Appl. No.: 11/883,487

(22) PCT Filed: Feb. 5, 2006

(86) PCT No.: PCT/IL2006/000143
§ 371 (c)(1), (2), (4) Date: May 29, 2008

(87) PCT Pub. No.: WO2006/082587
PCT Pub. Date: Aug. 10, 2006

(65) Prior Publication Data
US 2009/0125041 A1    May 14, 2009

Related U.S. Application Data

(60) Provisional application No. 60/649,128, filed on Feb. 3, 2005.

(51) Int. Cl.
*A61B 17/08* (2006.01)
*A61F 2/02* (2006.01)

(52) U.S. Cl.
USPC ........................................ 606/151; 623/23.72

(58) Field of Classification Search
USPC .......... 606/148, 151, 139, 213, 215; 604/523, 604/524, 525; 623/23.72
See application file for complete search history.

(56) References Cited

U.S. PATENT DOCUMENTS

| | | | |
|---|---|---|---|
| 5,368,602 A * | 11/1994 | de la Torre | 606/151 |
| 5,405,360 A | 4/1995 | Tovey | |
| 5,824,082 A * | 10/1998 | Brown | 623/11.11 |
| 6,099,518 A | 8/2000 | Adams et al. | |
| 6,592,602 B1 * | 7/2003 | Peartree et al. | 606/170 |
| 7,101,381 B2 * | 9/2006 | Ford et al. | 606/151 |
| 2006/0189918 A1 | 8/2006 | Barker | |
| 2007/0185506 A1 | 8/2007 | Jackson | |
| 2007/0260179 A1 | 11/2007 | Sholev et al. | |

FOREIGN PATENT DOCUMENTS

WO    WO 2009/104182    8/2009

OTHER PUBLICATIONS

International Search Report Dated May 29, 2008 From the International Searching Authority Re.: Application No. PCT/TL2006/000143.
Written Opinion Dated May 29, 2008 From the International Searching Authority Re.: Application No. PCT/IL2006/000143.
PolyTouch "Novel Deployment and Placement Device for Laparoscopic Ventral Hernia Repair", PolyTouch Medical Ltd., Misgav Venture Accelerator, 1 P., 2009.
International Preliminary Report on Patentability Dated Dec. 11, 2008 From the International Bureau of WIPO Re.: Application No. PCT/IL2006/000143.

* cited by examiner

*Primary Examiner* — Tuan V Nguyen

(57) ABSTRACT

A pre-rolled surgical mesh which allows its insertion to the abdominal cavity and having a comfortable lead and spread to a proper location. The pre-rolled mesh is double rolled from two opposite directions one toward the other. There is a device that holds, leads, releases and spreads the mesh in its proper location, related to the Hernia defect, and includes an element holds the double-rolled mesh, and allows its releasing; another element allows the spreading of the double-rolled mesh; additional element allows the leading and locating of the double-rolled mesh. A second shape assumed when spreading the mesh, as the center of the mesh matches the desired location, while the elements, which held and spread each side of the double rolled mesh had been released.

18 Claims, 7 Drawing Sheets

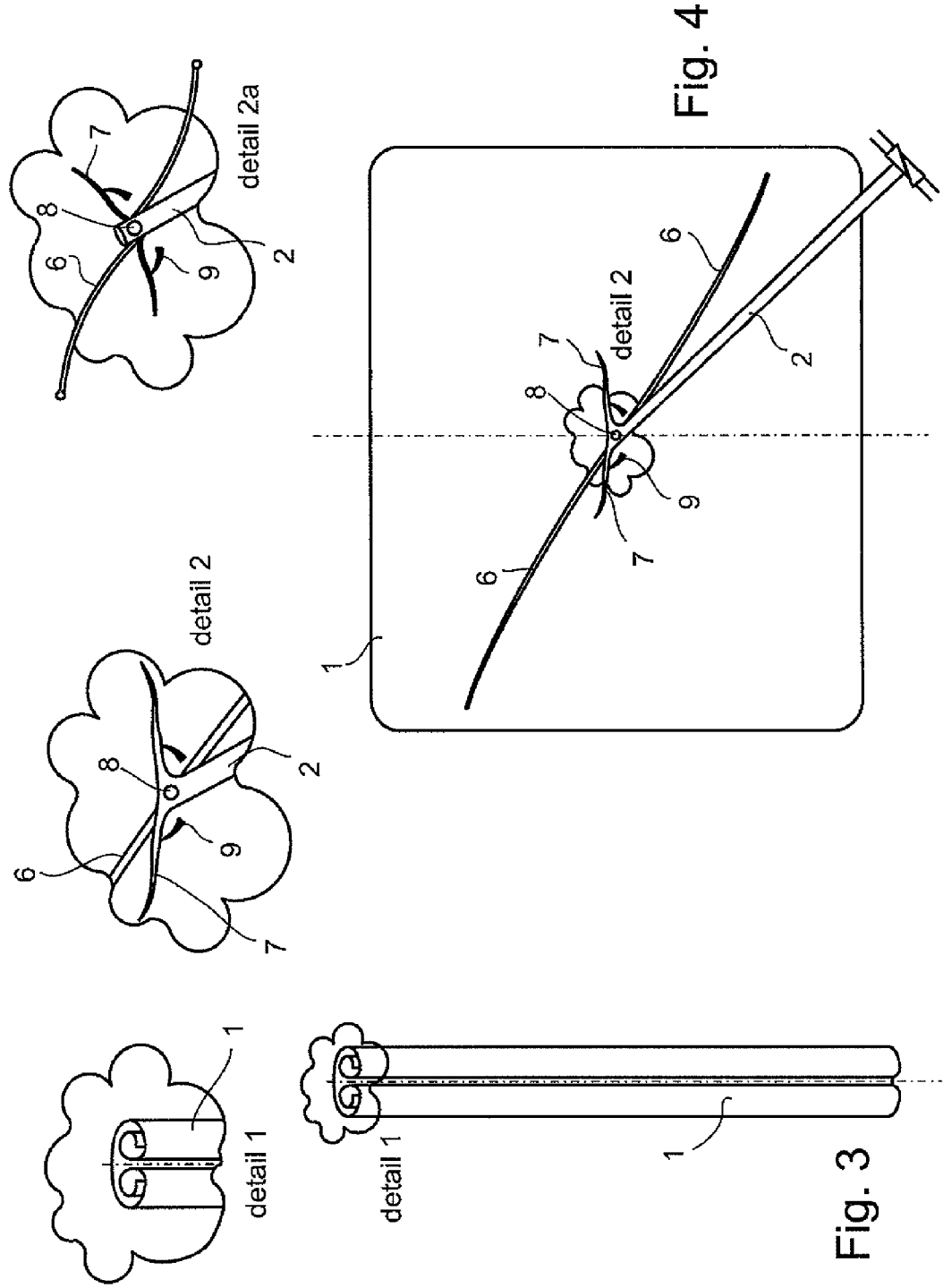

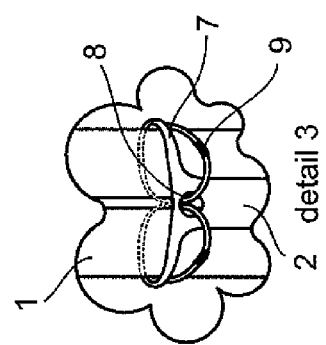
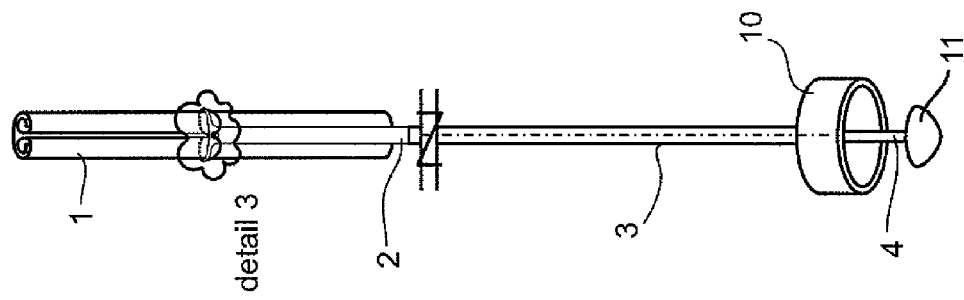
Fig. 6
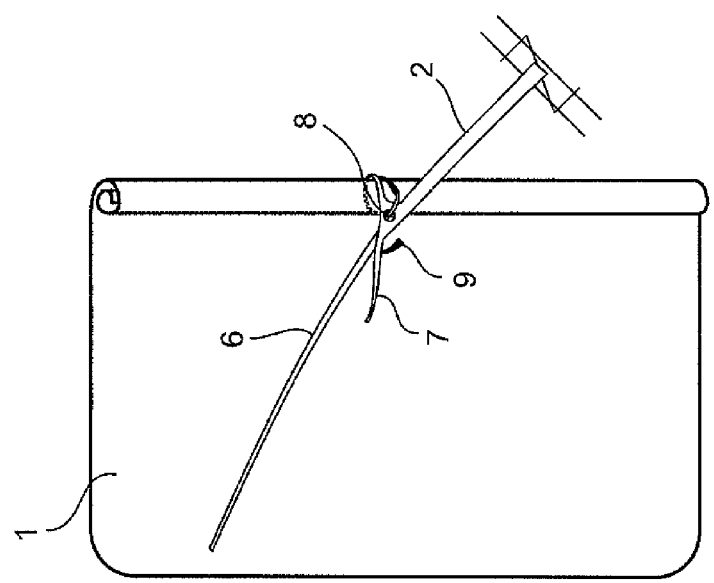
Fig. 5

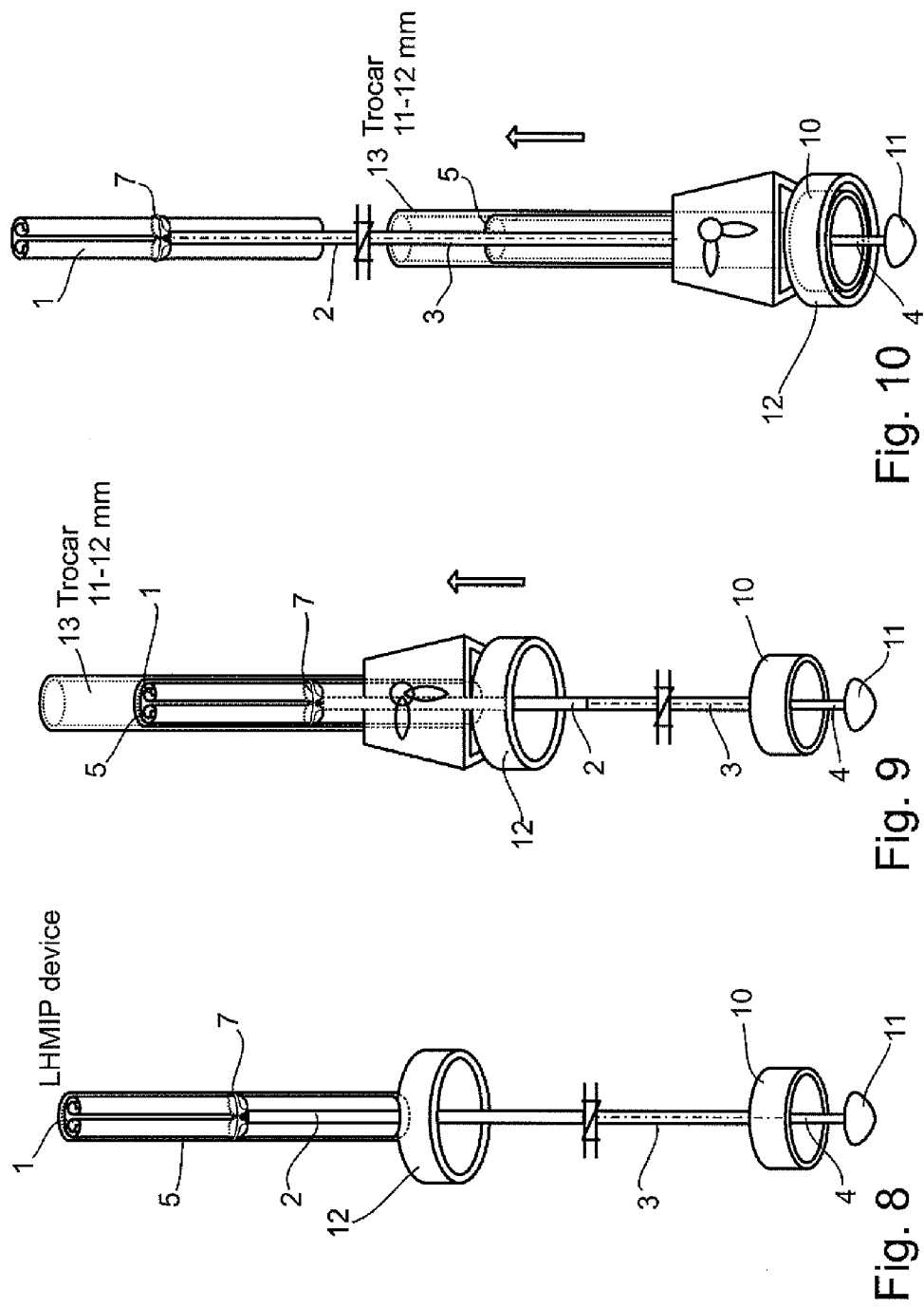

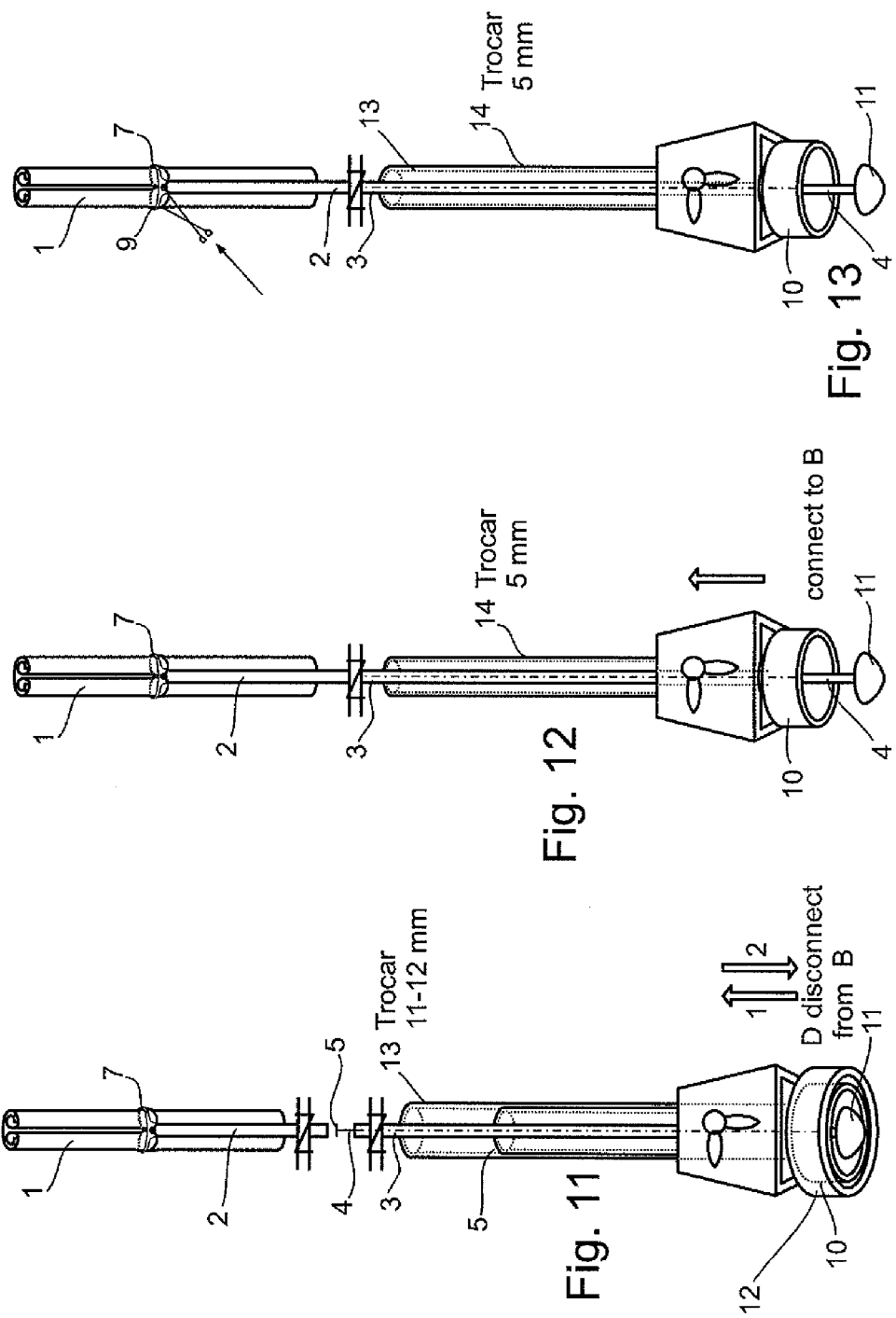

SURGICAL MESH, MESH INTRODUCING AND PLACING DEVICES AND METHODS

RELATED APPLICATIONS

This application is a National Phase of PCT Patent Application No. PCT/IL2006/00043 having International Filing Date of Feb. 5, 2006, which claims the benefit of U.S. Provisional Patent Application No. 60/649,128 filed on Feb. 3, 2005. The contents of the above Applications are all incorporated herein by reference.

FIELD AND BACKGROUND OF THE INVENTION

The present invention relates generally to surgical mesh, and in particular to the manner in which the mesh is pre-rolled, which allows its insertion to the abdominal cavity, and its comfortable lead and spread to its proper location, and to devices and methods of its application.

The surgical placement of the mesh, in Laparoscopy Groin (Inguinal) Hernia (GH) and Abdominal Wall Hernia (AWH), is the most crucial stage, difficult and complicated. This stage, which is the last one—adjusting the size of the mesh to the proper place—often finds the surgeon to be tired and short tempered. It includes a 'struggle' with the open, rebellious mesh in order to deliver it to its proper place, while the mesh itself hiding the centering of the hernia defect. It is truth for Diaphragmatic Hernia (DH) when a mesh is selected to be use.

Today, generally, surgeons form the mesh to a roll, and insert it to the abdominal cavity by a way of trocar. Some surgeons use a device which helps rolling the mesh and inserting it to the abdominal cavity. When the mesh is placed in the abdominal cavity, the surgeon will unroll it, and lead it by graspers to its proper location. In some cases, to ease the process of placing the mesh in its proper place on the abdominal wall, the surgeon will prepare in advance a few threads at the corners of the mesh, by with, will fixate by stitches the mesh to the abdominal wall. That is done to ease the process of placing, centering and fixating the mesh. Still, this procedure is difficult to execute, time consuming, and does not produce precise results.

There is thus a widely recognized need for, and it would be highly advantageous to have a device that allows executing the mentioned above stage easily, with efficiency, speed and precision, saving surgery time and preventing recurrence on account of improper locating for every average surgeon, not only a highly skilled one.

SUMMARY OF THE INVENTION

According to one aspect of the present invention, there is provided a surgical mesh, comprising:
a retracted, pre-rolled shape, adapted for insertion into an abdominal cavity, said pre-rolled shape being rolled from two opposite ends, towards each other;
 a first element, operative for maintaining said retracted, pre-rolled shape, and which, when activated, allows its deployment;
 a second element, adapted for opening and spreading said retracted, pre-rolled shape; and
 a third element adapted for positioning a leading edge of said mesh; and
a deployed shape, assumed when said mesh is positioned so that a center of said mesh is at a desired location, and said first element has been activated.

According to another aspect of the present invention, there is provided a pre-rolled mesh, comprising:
a first shape, adapted for insertion into the abdominal cavity and locating, and compromising:
 a mesh, double rolled from two opposite directions, one toward the other;
 an element holds the double-rolled mesh, and allows its releasing;
 another element allows the spreading of the double-rolled mesh;
 additional element allows the leading and locating of the double-rolled mesh;
a second shape, assumed when spreading the mesh, as the center of the mesh matches the desired location, while the elements, which held and spread each side of the double rolled mesh had been released.

According to still another aspect of the present invention, there is provided a pre-rolled mesh, comprising:
 a mesh, double rolled from two opposite directions, one toward the other;
According to second aspect of the present invention, there is provided a device that holds, leads, releases and spreads the mesh in its proper location, related to the Hernia defect, and comprising:
 an element holds the double-rolled mesh, and allows its releasing;
 another element allows the spreading of the double-rolled mesh;
 additional element allows the leading and locating of the double-rolled mesh.

According to an additional aspect of the present invention, the mesh can be made of PPP, or any other type of polymer, or any kind of patch, e.g. Dacron, PTFE, or any biological mesh or any combination of the above.

According to an alternative aspect of the present invention, the mesh is made from any kind of material.

According to an additional aspect of the present invention, the mesh can be rectangular, quadrangular, elliptic, oval, fenestrate or any other shape or form.

According to an additional aspect of the present invention, the mesh varies in sizes from 3-50 cm.

According to an additional aspect of the present invention, the mesh is double rolled along the vertical axis, such as preferred for Groin Hernia, or along the horizontal axis, such as preferred for Abdominal Wall Hernia, or along a diagonal axis, or both diagonal axes.

According to an additional aspect of the present invention, the elements that hold, spread and lead the double-rolled mesh can be connected in any combination, or not connected at all.

According to an additional aspect of the present invention, the elements that hold and spread the mesh can be made from plastic polymer, alloy, or any kind of metal—with or without memory shape.

According to an alternative aspect of the present invention, the elements that hold and spread the mesh are made from any kind of material.

According to an additional aspect of the present invention, the element that releases the double-rolled mesh can release both sides together, or separately.

According to an additional aspect of the present invention the element that holds the double-rolled mesh can be applied at the middle of the double-rolled mesh, or at any other point.

According to an additional aspect of the present invention, the spreading of the double-rolled mesh can result from the method of rolling, or the action provided by the spreading element, or the memory within the material of the mesh, or the surgeon's action of spreading, or any combination of the above at any rate.

According to another aspect of the present invention, there is provided an element that leads the double-rolled mesh to its correct position, comprising:

a long element that is connected to the holding element of the double-rolled mesh;

a method to connect and disconnect the long element from the holding element;

according to alternative aspect of the present invention the method of connecting and disconnecting the long element and the holding element, can be by a long pin going through the long element.

According to another aspect of the present invention, there is provided an element that acts as container and introducer of the double-rolled mesh.

According to an alternative aspect of the present invention the container element can have a form of cylinder with shoulders in diameter adapted to 5-18 mm Endoscopic trocar.

BRIEF DESCRIPTION OF THE DRAWINGS

The invention is herein described, by way of example only, with reference to the accompanying drawings. With specific reference now to the drawings in detail, it is stressed that the particulars shown are by way of example and for the purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description is taken with the drawings making apparent to those skilled in the art how the several forms of the invention may be embodied in practice.

In the drawings:

Figure 2:
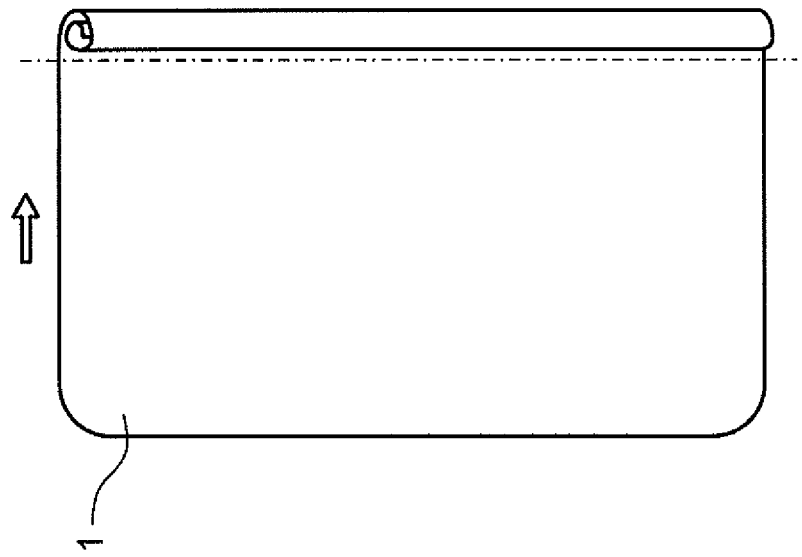
Figure 1:
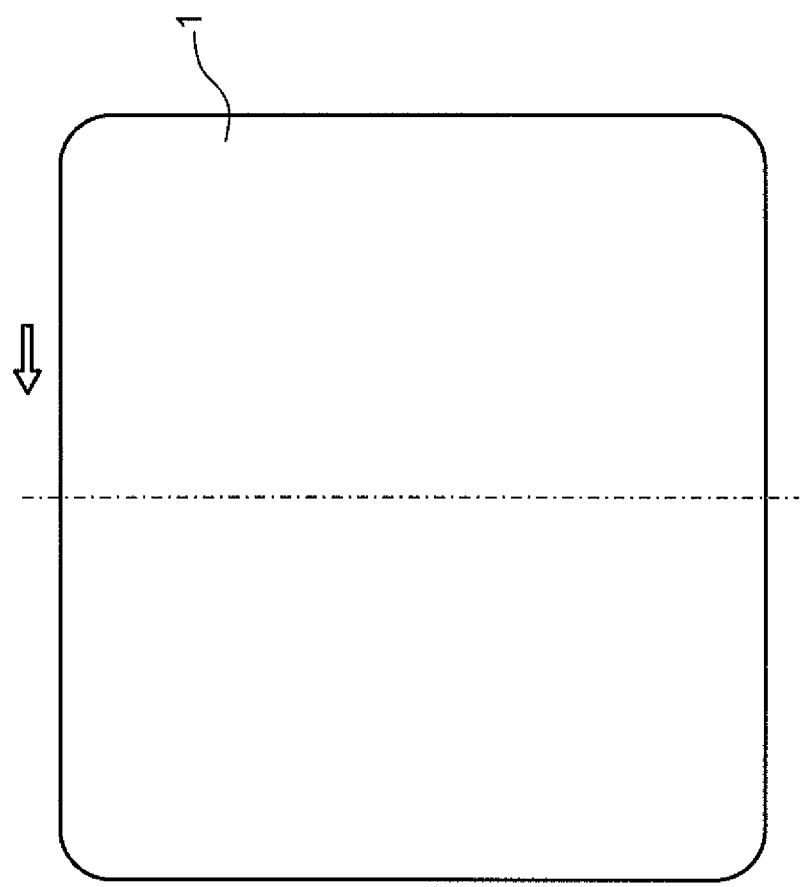
Figure 7:
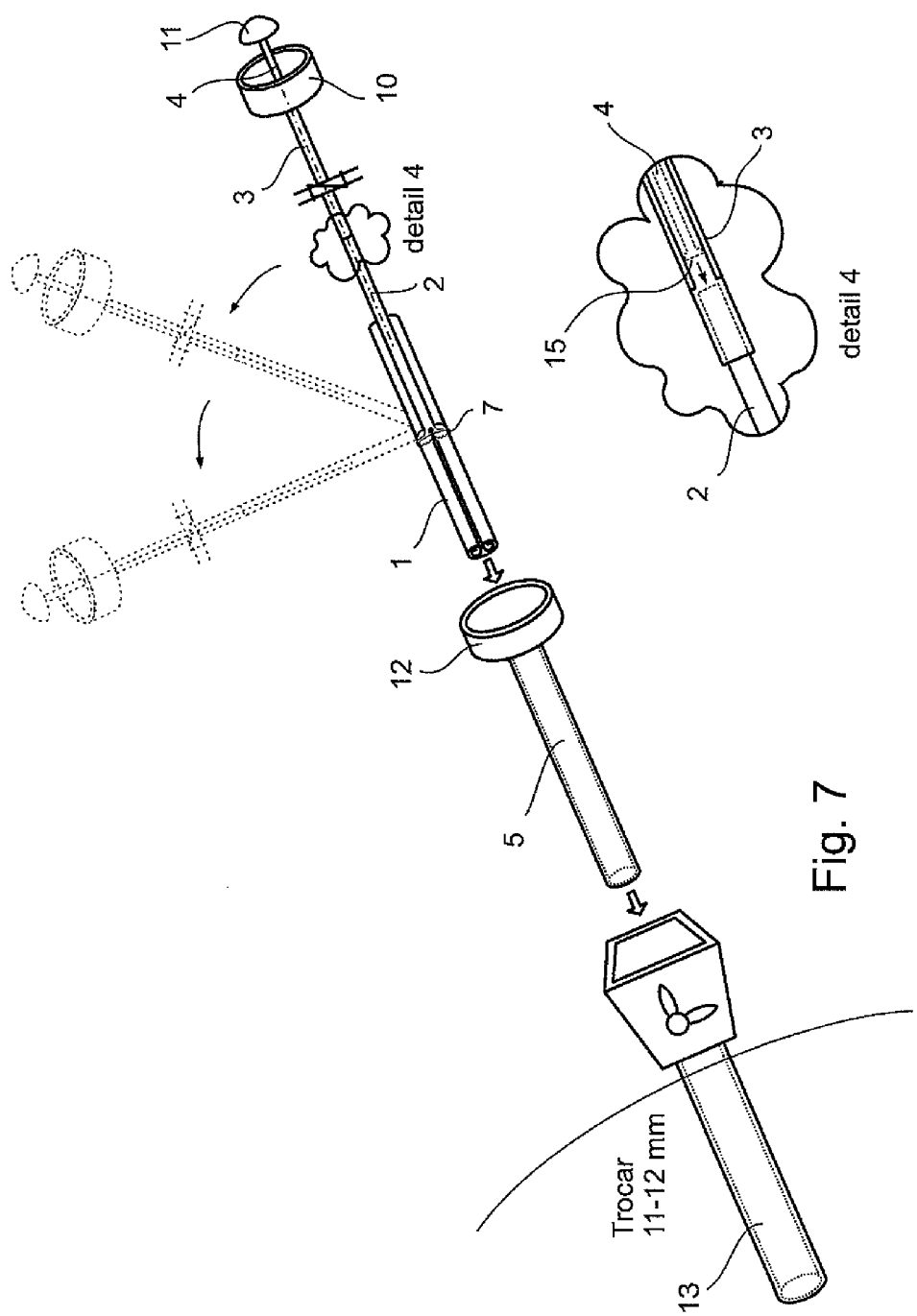

The various parts of the present invention with their listed letters are:

part 1—mesh
part 2—leading element
part 3—long rod
part 4—pushing pin
part 5—mesh container cylinder
part 6—spreading element
part 7—holding element
part 8—hole
part 9—breaking point of the holding element
part 10—shoulders of the long rod
part 11—button of the pushing pin
part 12—shoulders of the cylinder
part 13—11-12 mm trocar
part 14—5 mm trocar List of FIGURES:

FIG. 1 is a schematic illustration of the mesh (1) (in this specific case, for Inguinal Hernia), as known;

FIGS. 2-3 schematically illustrate the double-roll method, in accordance with the embodiment of the present invention;

DETAIL 1 is a magnification of the edge of the double-rolled mesh (1), as seen in FIG. 3, in accordance with the embodiment of the present invention;

FIG. 4 is a schematic illustration of the pre-rolled mesh (1), with all the elements that should be attached, in accordance with an embodiment of the present invention;

DETAIL 2 is a magnification of the different elements that should be attached to the mesh (1), in this specific case the holding element (7) and the spreading element (6) as extensions of the leading element (2) and made from the same materials, in accordance with the embodiment of the present invention;

DETAIL 2a is a magnification of the different elements that should be attached to the mesh (1), in this specific case the spreading element (6) is made from flexible metal wire and the holding element (7) is made from a different material, in accordance with the embodiment of the present invention;

FIG. 5 is a schematic illustration of the half-rolled mesh (1), with all the elements attached, in accordance with the embodiment of the present invention;

FIG. 6 is a schematic illustration of the double-rolled mesh (1), secured by the holding element (7), and attached by the leading element (2) to the long rod (3), in accordance with the embodiment of the present invention;

DETAIL 3 is a magnification of the secured double-rolled mesh (1) by the holding element (7), in accordance with the embodiment of the present invention;

FIG. 7 schematically illustrates the reversible attachment of the leading element (2) to the long rod (3) and the flexible connection of this whole complex to the double-rolled mesh (1). Also, is a schematic illustration of the placement of double-rolled mesh (1) into the cylinder container (5) and the insertion of all the above into the 11-12 mm trocar (13) that is already placed during surgery in the abdominal wall, in accordance with the embodiment of the present invention;

DETAIL 4 is a magnification of the connection between the leading element (2) and the long rod (3) and the location of the pushing pin (4) that will be later used for the release of the leading element (2) from the long rod (3), in accordance with the embodiment of the present invention;

FIG. 8 is a schematic illustration of the Laparoscopy Hernia Mesh Placement device —LHMP—assembled completely on all its parts, in accordance with the embodiment of the present invention;

FIGS. 9-15 schematically illustrates the operational manner in which the LHMP device ("the invention") is being used during surgery, in accordance with the embodiment of the invention.

DESCRIPTION OF THE PREFERRED EMBODIMENTS

The present invention is operative as an insertion contraption, which places a mesh after insertion, and devices and methods for its applications.

The principles and operation of the device and method according to the present invention may be better understood with reference to the drawings and accompanying descriptions.

Before explaining at least one embodiment of the invention in detail, it is to be understood that the invention is not limited in its application to the details of construction and the arrangements of the components set forth in the following description or illustrated in the drawings. The invention is capable of other embodiments or of being practiced of carried out in various ways. Also, it is to be understood that the phraseology and terminology employed herein is for the purpose of description and should not be regarded as limiting.

Here will be explained a one, specific example for the application of the present invention; furthermore, other applications to the present invention are possible. First will be described the stages of constructing the present invention, then, the method of using the present invention.

Refereeing to the drawings: The core of the present invention is the specific method of rolling the mesh—the double roll. Therefore, FIGS. 1-3 will schematically illustrate the rolling method, without referring to further elements of the present invention that will be explained, illustrate, and discuss in the rest of the drawings. FIG. 1 is a schematic illustration of the spread mesh (1). The mesh showed here is 15×12 cm, the one used for Groin Hernia. FIG. 2 is a schematic illustration of the rolling of the mesh. The mesh showed here is laid at the horizontal positioning, and the rolling is of the right side, from side toward the center. FIG. 3 is a schematic illustration of the already double-rolled mesh to the midline. DETAIL 1 of FIG. 3 is a schematic illustration of the end result of the double-rolled mesh.

Following will be described the double-rolling of the mesh (1) with the different elements. Referring further to the drawings, FIG. 4 schematically illustrates the position of the spreading element (6), fully extended, in its 'free' form after spreading the mesh (1). In this specific example, in a diagonal position, one side of the element positioned upwards and the other side positioned downwards, that for the purpose that when rolled with the mesh (1) will create a spiral, and not a bulk. DETAIL 2 of FIG. 4 schematically illustrates the spreading element (6) connected to the distal part of the leading element (2) as an extension of it, though it can be as well a flexible metal wire that is connected to the distal part of the leading element (2), as shown is DETAIL 2a of FIG. 4. Also shown in FIG. 4 is the holding element (7) that will be later referred to. In FIG. 5 schematically illustrates the mesh (1) that is rolled from side to center with the spreading element (6) within, and is held by the holding element (7), that is as well connected to the distal part of the leading element (2), though in a proximal positioning to the spreading element (6). It can also be from the same material of the leading element (2), or can be made from a different material. DETAIL 3 of FIG. 6 is a schematic illustration of the holding element (7), connected to the tip of the leading element (2), goes around each side of the double-roll, through the back of the mesh (1) itself and into the hole (8), and reconnects to itself to the breaking point of the holding element (9). The purpose of this is to establish a location that will be used to disengage the holding element (7) from the double-rolled mesh (1). That can be done in two ways. Either a. to create a 'breakage button' that will be held by a grasper and snap, or b. will be cut by scissors. FIG. 6 is a schematic illustration of the mesh (1) double-rolled from both sides to center, and is held by the holding element (7), as shown in DETAIL 3 of FIG. 6.

Referring further to the drawings, FIG. 7 is a schematic illustration of the leading element (2), in this specific case, 8 cm long, is connected to the long rod (3). DETAIL 4 of FIG. 7 is a schematic illustration of the form of connection between the proximal part of the leading element (2), that enters into the distal side of the long rod (3). In this specific case, the long rod (3) is 35 cm. In its proximal side there are shoulders (10) that prevent its sliding into the abdominal cavity. The pushing pin (4), with the button (11) in its end is inserted through the entire long rod (3). Push of the button (11) of the pin (4) by its distal part (15) through the long rod (3), will result in the disconnection of the leading element (2) plus the double-rolled mesh (1) that is connected to it. This connection, between the double-rolled mesh (1) to the leading element (2) is flexible, allowing a range of movement, as shown in FIG. 7.

Referring further to the drawings, FIG. 7 schematically illustrates the mesh container cylinder (5), in this specific case 11-12 mm in diameter that matches the diameter of the trocar (13). The cylinder (5) has shoulders (12) that act as a stopper to prevent the slide of cylinder (5) further into the trocar (13). The cylinder (5) is used as a container for the double-rolled mesh (1) plus its elements, as illustrated in FIG. 8.

Referring further to the drawings, FIG. 8 is a schematic illustration of the present invention assembled together, combining all the elements, named LHMP—Laparoscopic Hernia Mesh Placement.

METHOD OF USING THE DEVICE

Referring further to the drawings, FIGS. 8-15 schematically illustrate the operative procedure of the application of LHMP.

FIG. 8 is a schematic illustration of the 'ready-to-use' LHMP, combining all the elements, as a device.

FIG. 9 schematically illustrates the insertion of the device into the trocar (13), in this specific case 11-12 mm in internal diameter. This trocar is used during the surgery for the insertion of the laparoscopic scope of the camera. The scope is being pulled out for the purpose of insertion of the cylinder (5) into the trocar (13), when the shoulders (12) are being used as a stopper to prevent from the cylinder (5) to slip through the trocar (13) into the abdominal cavity.

FIG. 10 schematically illustrates the insertion of the double-rolled mesh (1) through the cylinder (5) into the abdominal cavity. The release is performed by the pushing of the long rod (3) with the help of the shoulders (10) that, as well, prevent the sliding of the long rod (3) into the abdominal cavity.

FIG. 11 schematically illustrates the disconnecting of the double-rolled mesh (1) with the elements attached to it from the long rod (3). This act is performed by pressing the button (11) of the pushing pin (4), causing the distal end of the pushing pin (15) to disconnect the leading element (2) from the long rod (3). As a result of that, the double-rolled mesh (1), with all its elements attached to it, is left placed on the bottom of the abdominal cavity. What remains in the trocar (13) is the pushing pin (4), inside the long rod (3), inside the cylinder (5). All of the above is being pulled together out of the trocar (13), and the scope of the camera is being inserted back into the trocar (13).

FIG. 12 is a schematic illustration of the pushing pin (4), inside the long rod (3), which has been replaced as a unit inside a different trocar (14), in this specific case 5 mm in inner diameter. This thinner trocar (14) has already been placed laterally to the central 11-12 mm trocar (13). Under the supervision of the camera, and with the help of an endoscopic grasper, the leading element (2) is being held by the grasper, lead to the long rod (3) and the two are being reconnected.

At this stage, the double-rolled mesh (1) is in the abdominal cavity, the leading element (2)—which has just been reconnected to the long pin (3)—is attached to the exact center, horizontal and vertical, of the double-rolled mesh (1). This point of connection has been chosen in this manner to ease the placement and centering of the double-rolled mesh (1) and provide the most comfortable way of controlling the maneuvering of the double-rolled mesh (1) to its proper placement at the center of the defect. (In the example before us the mesh is double rolled toward the vertical center line, suitable for repair of Groin hernia, whereas in Abdominal Wall hernia repair the mesh is double rolled toward the horizontal center line.)

Under the supervision of the camera, the double-rolled mesh (1) is now in place over the center of the defect, vertically. FIG. 13 schematically illustrates the cutting of the holding element (7) from itself, by a breakage point (9) or by scissors, resulting in the releasing of one side of the double-rolled mesh (1).

Figure 14:
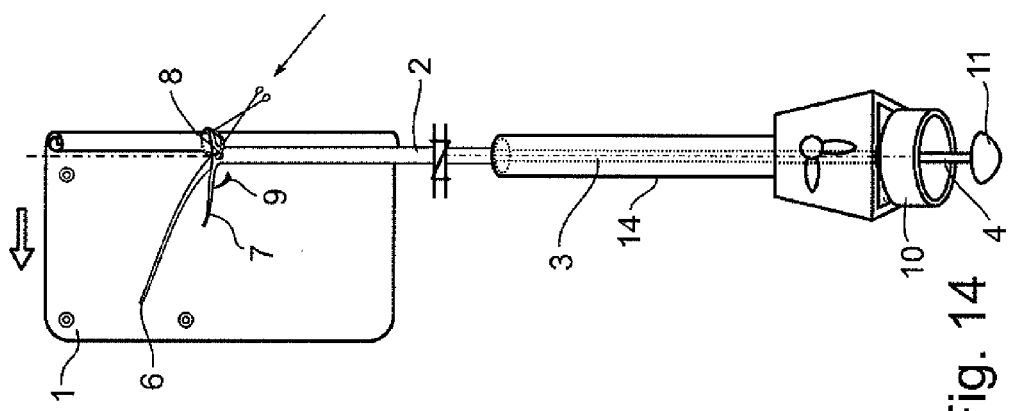

FIG. 14 is a schematic illustration of the spreading of one roll of the double-rolled mesh (1). This stage is being carried out—and due to the fact that the holding element (7) was cut—by the fact that the spreading element (6) that was rolled within the mesh is straightens, due to its material memory, or flexibility. If there is a need to complete the spreading of the mesh, the surgeon can do that with the help of the grasper, since the mesh is being held at its place. The spread side of the mesh is being fixed to the abdominal wall by surgical staples, as needed.

The same process is being applied to the other roll of the mesh; the cutting of the holding element (7), the release of the roll, the spreading of the mesh (1) and the fixation to the abdominal wall. Throughout the mentioned above process (of both sides of the mesh) the device is kept in its place, since the two arms of the spreading element (6) help keep the mesh (1) in its proper place.

Figure 15:
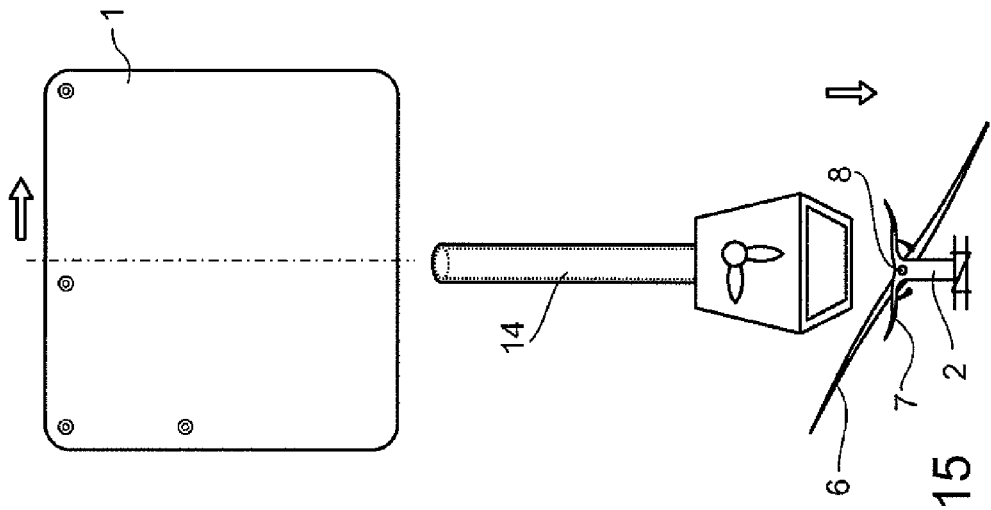

FIG. 15 is a schematic illustration of the mesh (1) spread in its entire and fixed to the abdominal wall. The entire device (elements 2, 3, 4, 6, 7) is being withdrawn out of the abdominal cavity, through the trocar (13), by pulling out the long rod (3). Since the flexibility of the spreading element (6) and of the holding element (7), and the fact that they are both connected to the leading element (2), this stage is being carried out effortlessly.

What is claimed is:

1. A surgical placement device for placing a surgical mesh structure, comprising:
    a positioning element;
    at least one self-straightening element mounted on said positioning element and includes at least one arm, said at least one arm is removably attached to a surgical mesh structure which is rolled with the at least one self-straightening element in a collapsed state within, wherein the at least one self-straightening element is adapted to self-straighten so as to spread and deploy the surgical mesh while being fully inserted in the subject; and
    at least one holding element adapted for preventing the self straightening of the at least one self-straightening element, wherein neutralization of the at least one holding element releases a force in the at least one self-straightening element in the collapsed state; and
    wherein said at least one holding element is operative for maintaining said rolled surgical mesh structure rolled with the at least one self-straightening element in said collapsed state within before activated and to allow deployment of said rolled surgical mesh structure when activated.

2. The surgical placement device of claim 1, wherein the at least one holding element in the collapsed state is adapted for maintaining the surgical mesh structure rolled from two opposite ends into a double-scroll structure having two separate scrolls; wherein said at least one holding element is operative for maintaining said rolled surgical mesh in said double-scroll structure before activated and to allow deployment of each said scroll when activated.

3. The surgical placement device of claim 2, wherein the maintaining comprises separately maintaining each of the scrolls in the double-scroll structure so as to allow a separate deployment of each the scroll.

4. The surgical placement device of claim 1, wherein said positioning element adapted for positioning the surgical mesh prior to deployment.

5. The surgical placement device of claim 4, wherein the positioning element is adaptable to alter its angular positioning with respect to the surgical mesh structure during positioning of the surgical mesh structure.

6. The surgical placement device of claim 4, wherein the positioning element is adapted to be repeatedly engaged and disengaged.

7. The surgical placement device of claim 1, wherein said surgical placement device shaped and adapted for insertion into a body cavity and to release said surgical mesh structure onto a member of a group consisting of groin inguinal, abdominal wall, and diaphragmatic hernia.

8. The surgical placement device of claim 1, wherein at least a leading element of said surgical placement device is sized and shaped for insertion into a body cavity for laparoscopic or endoscopic procedures.

9. The surgical placement device of claim 1, wherein said at least one arm is made of a flexible wire.

10. The surgical placement device of claim 9, wherein the wire includes shape memory wire.

11. The surgical placement device of claim 1, wherein the at least one self-straightening element is made from a material selected from a group including: plastic polymer, alloy and metal.

12. The surgical placement device of claim 1, wherein the positioning element is operable to be engaged to a central area of the surgical mesh structure including edges of the surgical mesh.

13. The surgical placement device of claim 12, wherein the positioning element is engaged to a horizontal and a vertical center of the surgical mesh structure.

14. The surgical placement device of claim 1, wherein the positioning element adapted for positioning the surgical mesh structure is fixedly attached to the at least one self-straightening element.

15. The surgical placement device of claim 1, wherein the surgical mesh structure has a size from 3-50 cm.

16. The surgical placement device of claim 1, adapted to be inserted through a body cavity of the subject.

17. The surgical placement device of claim 1, wherein said surgical mesh structure is inserted into a cylinder container, said cylinder container is used as a container for said surgical mesh structure.

18. The surgical placement device of claim 1, wherein the at least one holding element is connected to the positioning element.

* * * * *